United States Patent [19]
Wyatt et al.

[11] Patent Number: 5,201,717
[45] Date of Patent: Apr. 13, 1993

[54] SAFETY ENCLOSURE

[76] Inventors: Philip Wyatt, 1018 Marengo Dr., Glendale, Calif. 91206; Gary Schaeffer, 25428 Via Escovar, Valencia, Calif. 91355; Eli Shemesh, 31 Shave-Tzion St. P.B. 6675, Ashdod 77100, Israel

[21] Appl. No.: 622,868

[22] Filed: Dec. 5, 1990

[51] Int. Cl.$^5$ .................................................. A61M 5/32
[52] U.S. Cl. ................................... 604/192; 604/905; 604/201; 128/912
[58] Field of Search ............... 604/110, 167, 171, 192, 604/201, 263, 283, 284, 82–86, 88, 905; 128/912, 919

[56] References Cited

U.S. PATENT DOCUMENTS

| | | | |
|---|---|---|---|
| 2,857,912 | 10/1958 | Feinstone et al. | 604/192 |
| 3,512,524 | 5/1970 | Drewe | 604/192 |
| 3,989,044 | 11/1976 | Meierhoefer | 604/192 |
| 4,232,669 | 11/1980 | Nitshke | 604/263 |
| 4,281,653 | 8/1981 | Barta et al. | 604/192 |
| 4,673,400 | 6/1987 | Martin | 604/283 |
| 4,735,311 | 4/1988 | Lowe et al. | 604/198 |
| 4,752,292 | 6/1988 | Lopez et al. | 604/283 |
| 4,784,650 | 11/1988 | Coburn | 604/272 |
| 4,834,716 | 5/1989 | Ogle, II | 604/192 |
| 4,883,470 | 11/1989 | Haindl | 604/192 |
| 4,923,445 | 5/1990 | Ryan | 604/198 |
| 4,927,018 | 5/1990 | Yang et al. | 604/263 |
| 4,946,445 | 8/1990 | Lynn | 604/283 |
| 4,950,260 | 8/1990 | Bonaldo | 604/283 |
| 4,964,855 | 10/1990 | Todd et al. | 604/283 |
| 4,969,883 | 11/1990 | Gilbert et al. | 604/88 |
| 4,981,469 | 1/1991 | Whitehouse et al. | 604/86 |

OTHER PUBLICATIONS

Kendall McGaw Laboratories, Inc.–Flyer Y08-54-0-209 (Apr. 1990).
Kendall McGaw Laboratories, Inc.–Flyer Y08-52-0-201 (Jan. 1990).
Abbott Laboratories–Flyer 87-343-15 (Dec. 1987).

*Primary Examiner*—C. Fred Rosenbaum
*Assistant Examiner*—Ronald Stright, Jr.
*Attorney, Agent, or Firm*—James E. Brunton

[57] ABSTRACT

An enclosure for use with an injection site in which the penetrating member, such as a needle, is at all times maintained within a protective shroud that protects the user from accidental needle sticks and contamination during use.

11 Claims, 6 Drawing Sheets

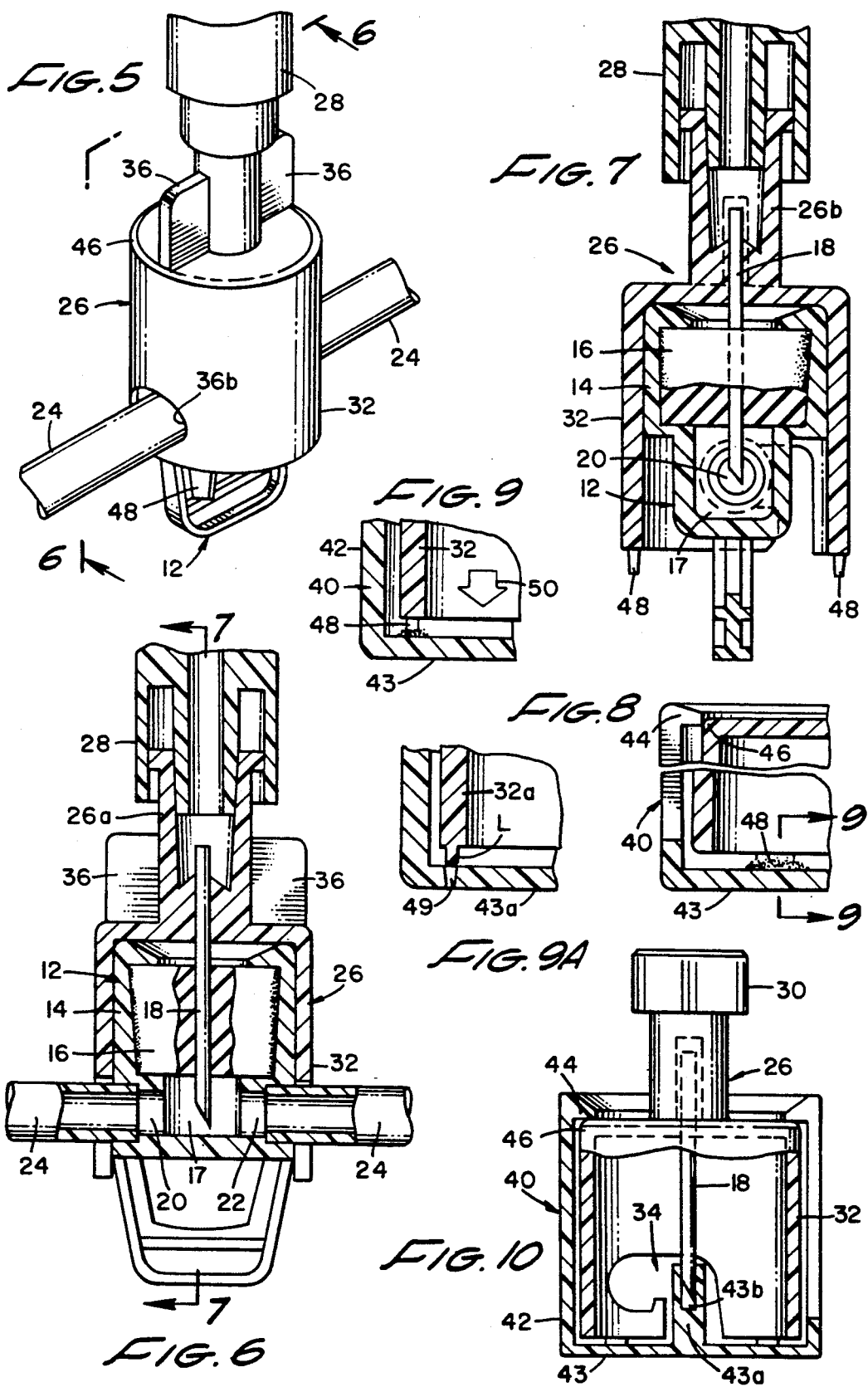

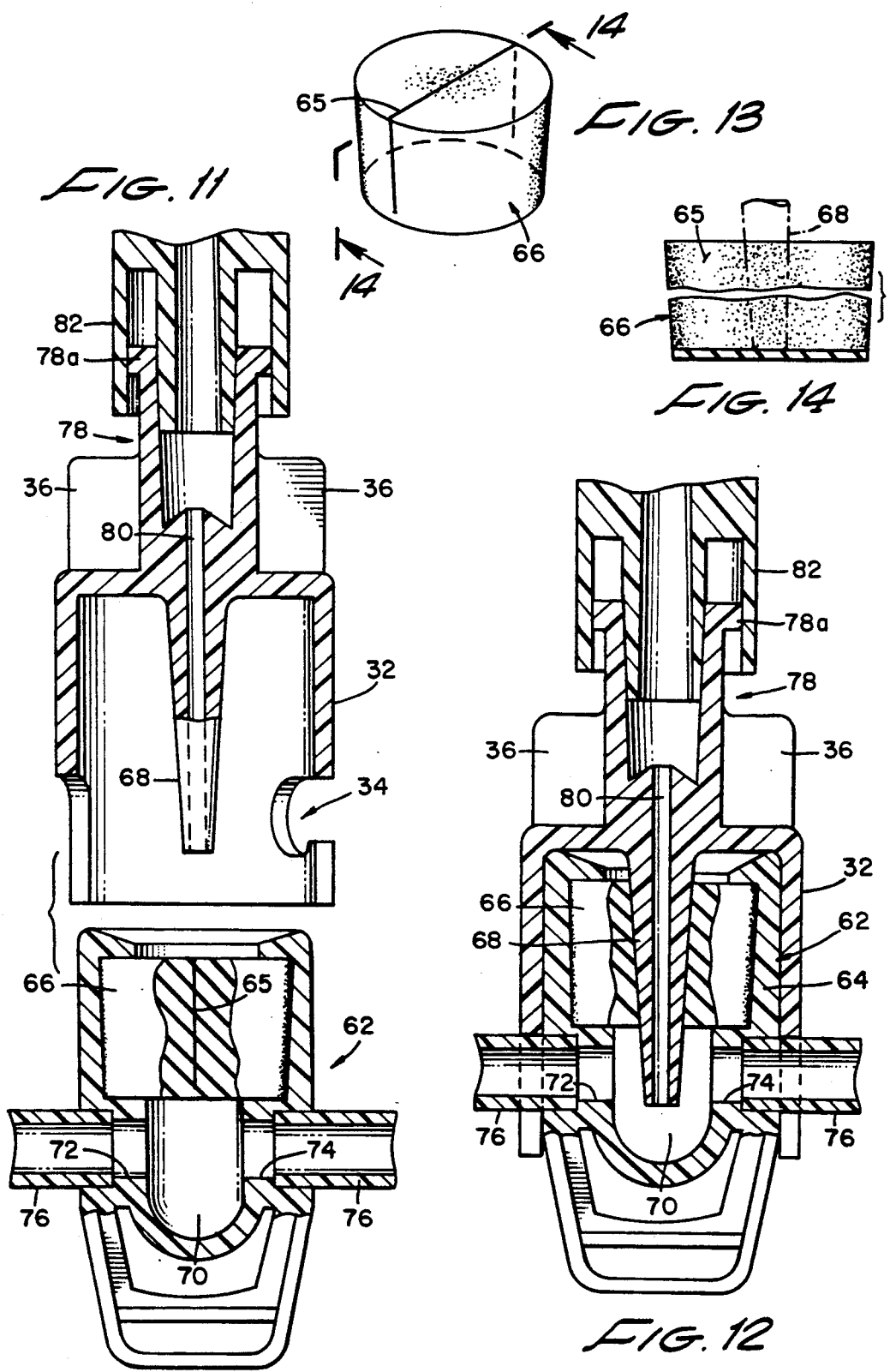

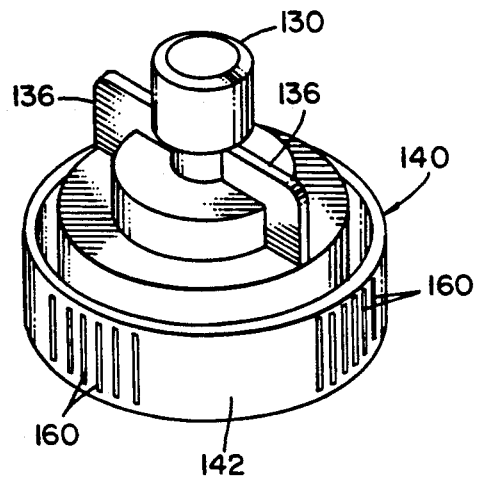
FIG. 15
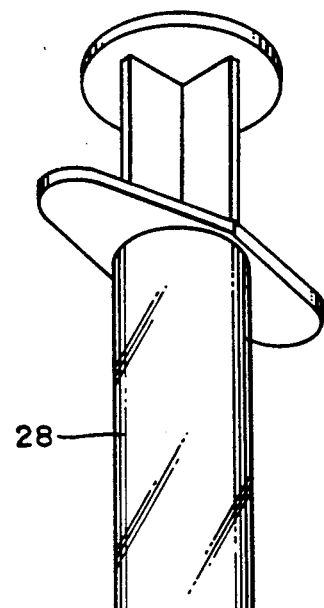
FIG. 20
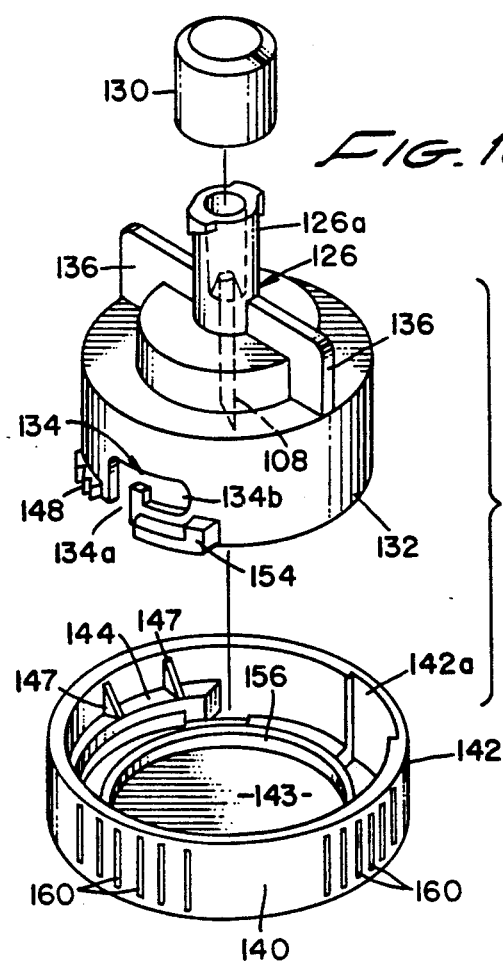
FIG. 16
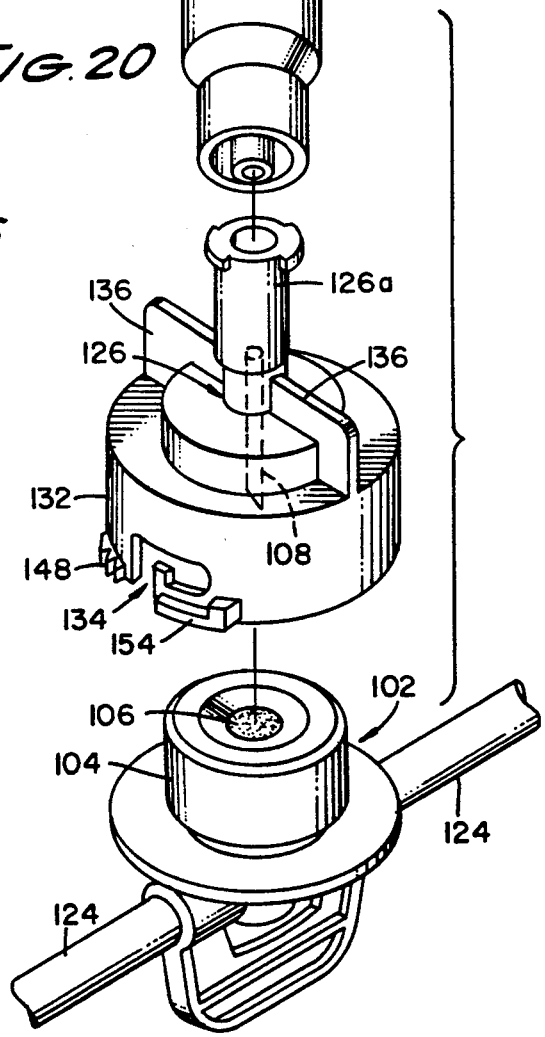

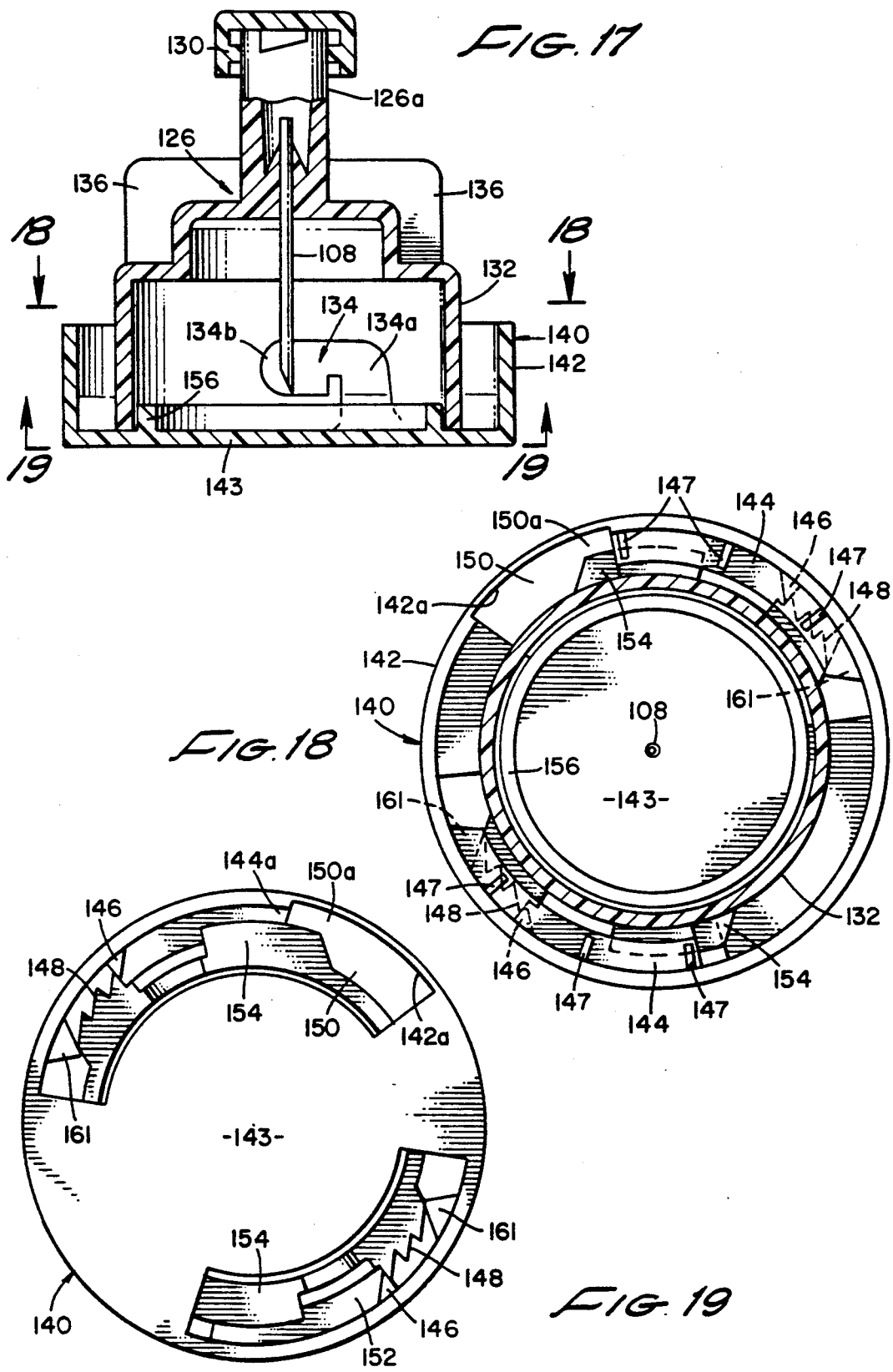

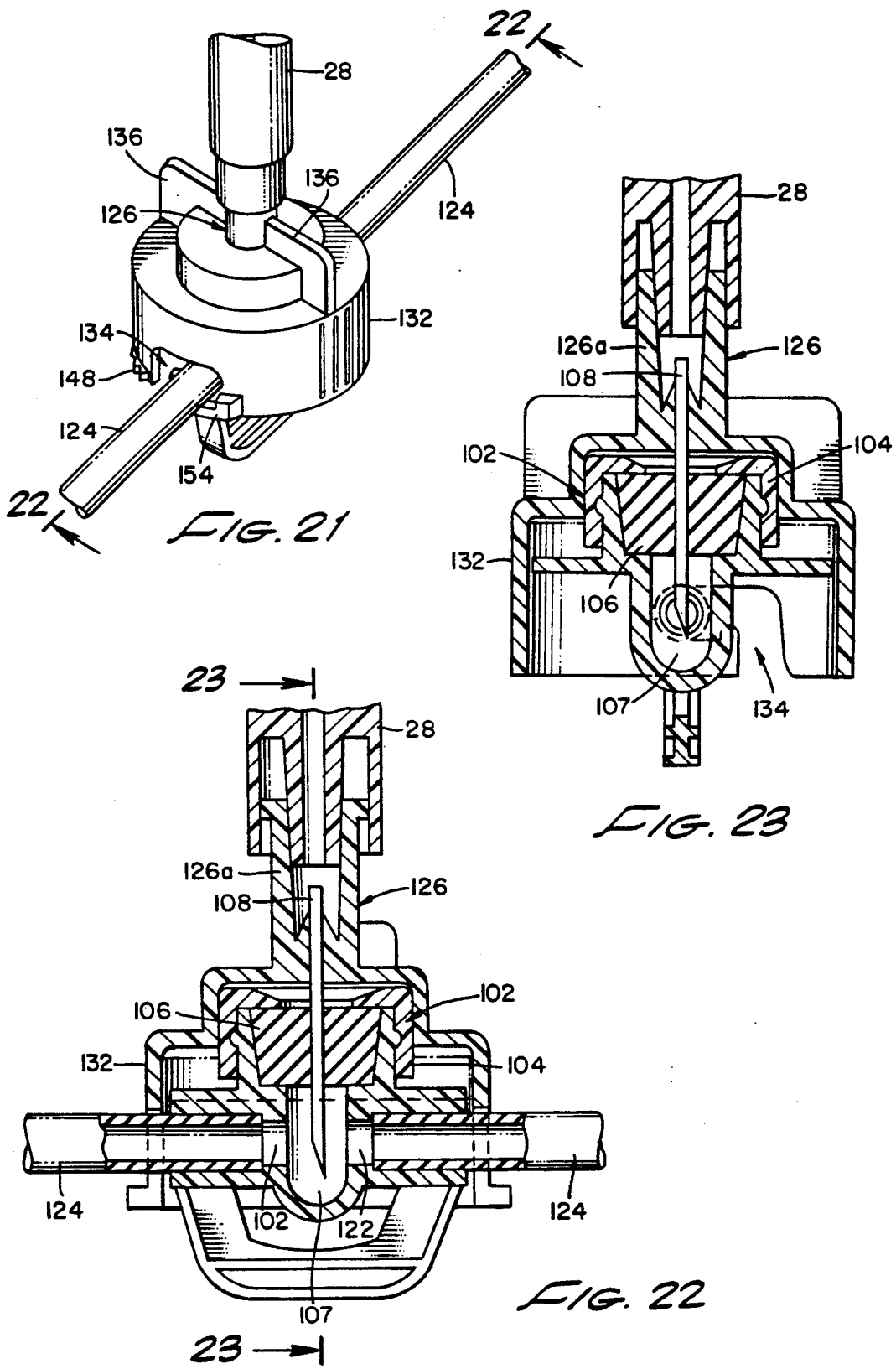

SAFETY ENCLOSURE

BACKGROUND OF THE INVENTION

1. Field of the Invention

The present invention relates generally to medical infusion and fluid sampling devices. More particularly, the invention concerns a safety enclosure for enclosing a hollow member, such as a hypodermic needle, or blunt cannula adapted for use with one or more injection sites disposed between two lengths of small plastic tubing.

2. Discussion of the Invention

Needle sticks have become an extremely serious problem. Approximately 40 percent of all pharmaceuticals used in hospitals are now administered by injection, either directly or through injection sites. Similarly, blood or other fluid sampling using hypodermic syringes and evacuated chambers has become common place. Accordingly, health-care workers are continuously exposed to needle sticks and to contaminated blood. Statistics show that most needle sticks occur during recapping of used needles, picking up and carrying the needle, placing needles in a receptacle, or when needles are inadvertently left at a patient's bedside.

Hepatitis-B has long been of great concern to clinicians. This concern was meaningfully addressed only after the recent epidemic of acquired immune deficiency syndrome (AIDS). As pointed out in the Aug. 4, 1988 issue of the *New England Journal of Medicine*, 319:284–288, the epidemic of the acquired immunodeficiency syndrome has led to great concern among health-care workers about all of the various risks they face in the hospital environment. Needle-stick injuries, in particular, have drawn attention, for despite safety guidelines and employee education, there is little evidence that their incidence is abating. While transmission of human immunodeficiency virus is unusual after a needle stick, nevertheless, infections in health-care workers have been attributed to this type of exposure. The potential medical and psychological consequences of needle sticks for health-care workers and their spouses or sexual partners remain great.

Studies concerning needle-stick injuries indicate that disposable syringes accounted for about 35 percent of the injuries and needle assemblies for another 26 percent. These types of devices are typically used in connection with the methods and apparatus for fluid administration and blood or other fluid sampling. More particularly, these types of devices are used in connection with an apparatus for arterial and venous blood sampling of the character sold by Abbott Laboratories of Mountain View, Calif., Telos Medical of Upland, Calif., or Concord/Portex of Keene, N.H. Additionally, one form of the device of the invention is uniquely usable with an improved apparatus for arterial and venous blood sampling invented by the present inventor and described in U.S. Pat. No. 4,763,648.

Each of the commercially devices described in the preceding paragraph comprises an injection site including a body having a fluid chamber and spaced apart fluid ports adapted to be connected to plastic tubing. The upper chamber is adapted to be sealed by a septum penetratable by a penetration member such as a blunt cannula or a needle of a syringe. As will be better understood from the description which follows, the device of the present invention is usable with the devices of the character just described and uniquely carries a penetration member disposed interiorly of a novel shroud portion which is adapted to be closely received over the body of the injection site and interlocked to the tubing. Following the injection or sample step, the skirt portion can be quickly unlocked from the tubing, removed from the body and safely sealed by a novel interlocking closure cap.

SUMMARY OF THE INVENTION

It is an object of the present invention to provide an enclosure for use with an injection site in which the penetrating member, such as a needle, is at all times maintained within a protective shroud that protects the user from accidental needle sticks and contamination during use.

Another object of the invention is to provide an enclosure of the aforementioned character in which, after use, the penetrating member can be completely encapsulated within the shroud by a non-removable cap which can be positively interconnected to the shroud.

Another object of the invention is to provide a device of the character described in the preceding paragraph in which the cap, once connected to the shroud, is irremovably locked in position.

Another object of the invention is to provide an enclosure of the type described herein which can be readily fit over the injection site and be removably locked to the plastic tubing that connects the injection site with the patient.

Another object of the invention is to provide an enclosure of the class described which can be molded from a light weight, durable yet transparent plastic material which permits visualization of the cannula to enable proper alignment during use of recapping.

Still another object of the invention is to provide an enclosure of the character described in the preceding paragraphs which is easy to use with a minimum of training being required.

Another object of the invention is to provide an enclosure of the class described which can be very inexpensively manufactured in large volume.

BRIEF DESCRIPTION OF THE DRAWINGS

FIG. 5 is a generally perspective view similar to FIG. 4, but showing the apparatus of the invention superimposed over the injection site and interlocked with the plastic tubes communicating therewith.

FIG. 6 is a cross-sectional view taken along lines 6—6 of FIG. 5.

FIG. 7 is a cross-sectional view taken along lines 7—7 of FIG. 6.

FIG. 8 is a fragmentary cross-sectional view similar to FIG. 3, but illustrating movement of the closure cap of the invention toward a locked position with the crushable feet of the shroud portion of the device being crushed by the inner surfaces of the closure cap during the interlocking step.

FIG. 9 is a fragmentary cross-sectional view taken along lines 9—9 of FIG. 8 further illustrating the crushing of the supports.

FIG. 9A is a fragmentary cross-sectional view of an alternate form of cap and skirt structure.

FIG. 10 is a side elevational view partly in cross-section similar to FIG. 3, but showing the closure cap in a fully locked position.

FIG. 11 is a side elevational, exploded view, partly in cross-section illustrating another form of injection site and apparatus of the present invention in which the penetrating means is provided in the form of a blunt cannula.

FIG. 12 is a side elevational view partly in cross-section similar to FIG. 11, but showing the apparatus of the invention interlocked with the tubing leading toward the injection site.

FIG. 13 is a generally perspective view of the septum of the second form of injection site wherein a diametrically extending slit is provided in the septum to accept the blunt cannula.

FIG. 14 is a fragmentary cross-sectional view taken along lines 14—14 of FIG. 13.

FIG. 15 is a generally perspective view of still another embodiment of the present invention.

FIG. 16 is an exploded, generally perspective view of the apparatus of FIG. 15.

FIG. 17 is a cross-sectional view taken along lines 17—17 of FIG. 15.

FIG. 18 is a cross-sectional view taken along lines 18—18 of FIG. 17.

FIG. 19 is a cross-sectional view taken along lines 19—19 of FIG. 17.

FIG. 20 is an exploded, generally perspective view of the apparatus of the invention illustrating the manner of its use in connection with the type of injection site described in U.S. Pat. No. 4,763,648.

FIG. 21 is a generally perspective view similar to FIG. 20, but showing the apparatus of the invention superimposed over the injection site and interlocked with the plastic tubes communicating therewith.

FIG. 22 is a cross-sectional view taken along lines 22—22 of FIG. 21.

FIG. 23 is a cross-sectional view taken along lines 23—23 of FIG. 22.

DESCRIPTION OF THE INVENTION

Figure 1:
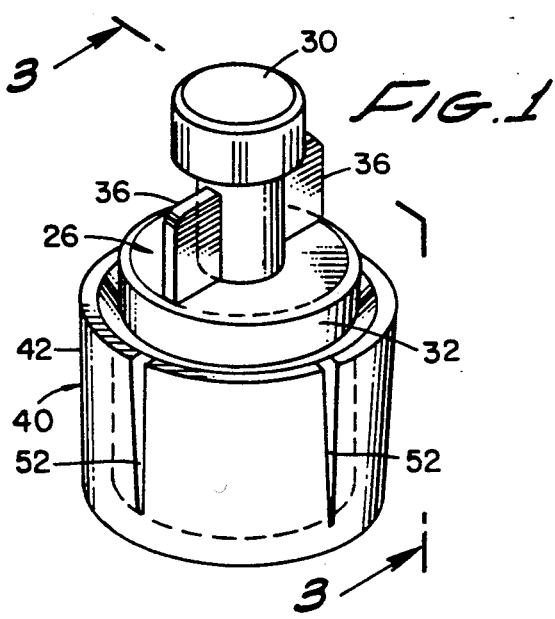
FIG. 1 is a generally perspective view of one embodiment of the present invention.

Referring to the drawings and particularly to FIGS. 1 through 6, one form of the safety enclosure of the present invention is there illustrated. This form of the enclosure is designed for use in conjunction with an injection site 12 of the character shown in FIG. 4 which is a low profile small volume site that comprises a body portion 14 within which is mounted a septum 16. As best seen in FIG. 6 body portion 14 includes a flat bottom, low volume hollow chamber 17 which is accessible via the septum by a penetrating means such as a hollow needle 18. Chamber 17 has first and second ports 20 and 22 each of which is connected to a length of tubing 24. As previously mentioned, injection site 12 is of a character well known to those skilled in the art as, for example, the injection site sold by Abbott Laboratories, Telos Medical or Concord/Portex. The apparatus of the invention can, of course, also be used with other injection sites of comparable configuration.

The embodiment of the safety enclosure illustrated in FIGS. 1 through 10, comprises supporting means, generally designated by the numeral 26, for rigidly supporting the penetrating means such as penetrating member comprising hollow needle 18 of standard design having a central fluid passageway. Operably associated with the supporting means for conducting fluid toward and away from the fluid passageway of needle 18 is a fluid flow means shown in FIGS. 6 and 20 as a syringe of well-known construction, the lower end of which is sealably receivable within the generally tubular shaped upper end 26a of supporting means 26. Prior to and following use of the device of the invention, the upper end 26a of the closure means can be closed by a removable cap 30 of the character shown in FIGS. 1 and 2.

The lower portion of the supporting means 26 comprises enclosure means for enclosing needle 18 and for releasably interconnecting the device with the lengths of tubing 24 which lead to the injection site 12. The enclosure means is here provided in the form of a skirt-like shroud 32 having oppositely disposed, bayonet-like, P-shaped, tube-receiving apertures 34. Apertures 34 have a axially-extending leg portion 34a which is in communication with a curved portion 34b. Portions 34a and 34b, which comprise the interconnection means of the invention for interconnecting the device to the tubes 24, are sized so that tubes 24 can be closely received first within leg portions 34a and, then upon rotation of the skirt portion, within curved portions 34b in a manner to releasably interlock the device with tubes 24. Disposed intermediate upper portion 26a and skirt portion 32 is a pair of oppositely disposed, outwardly-extending gripping members 36 which can be gripped by the fingers of the user to facilitate rotation of the apparatus into the locking position shown in FIG. 5.

Forming an important feature of the apparatus of the invention is closure means for encapuslating the shroud portion of the enclosure means in a manner to completely and safely enclose the penetrating member such as needle 18, which may be contaminated after the sampling operation. In the present form of the invention, the closure means comprises a cup-like member 40 having interconnected side and bottom walls 42 and 43 respectively (FIG. 10). Provided on wall 42 is a circumferentially extending rim 44 which comprises the locking means of the present invention for permanently interlocking the closure means with supporting means 26. Provided on wall 43 is an integrally formed upstanding column 43a having a counterbore 43b the purpose of which will presently be described.

Figure 3:
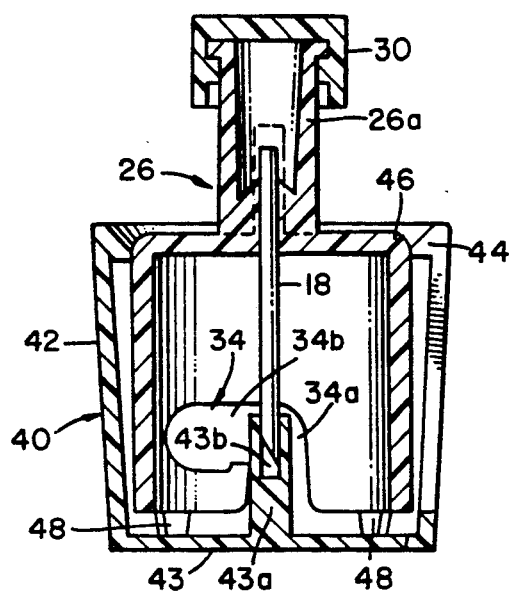
FIG. 3 is a cross-sectional view taken along lines 3—3 of FIG. 1.
Figure 2:
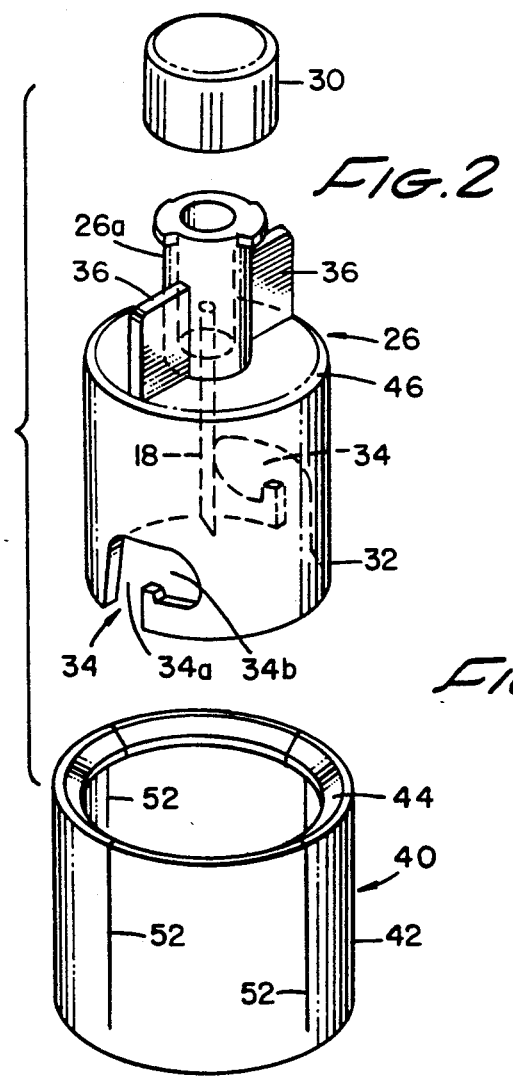
FIG. 2 is an exploded, generally perspective view of the apparatus of FIG. 1.
Figure 4:
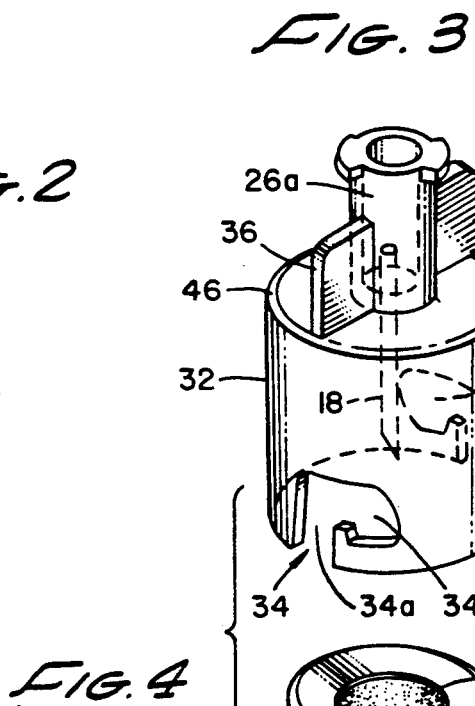
FIG. 4 is an exploded, generally perspective view of the apparatus of the invention illustrating the manner of its use in connection with an injection site.

As best seen in FIG. 10 the enclosure means portion of the device is provided with a circumferentially extending shoulder 46 over which locking rim 44 can be snapped when shroud 32 is inserted into the closure cap in the manner shown in FIG. 3. To prevent accidental interlocking of the closure cap with shroud 32 spacer means, shown here as crushable legs 48, are provided on the lower edge of the shroud (FIG. 3). Legs 48 normally prevent interlocking of the closure cap and the shroud. However, when a sufficient force is exerted on the shroud in the direction of the arrow 50 shown in FIG. 9, legs 48 will crush, or collapse, in the manner illustrated allowing locking rim 44 to snap over shoulder 46. To facilitate the interlocking step walls 40 of the enclosure means can be provided with slits 52 of the character shown in FIG. 2 which permit the walls to flex outwardly.

FIG. 9A shows an alternate form of the apparatus in which shroud 32a is provided with downwardly depending locking means shown here as legs L which are lockably receivable within tapered apertures 49 provided in bottom wall 43a. With this form of the device, a downward pressure on the enclosure means will cause legs L to be press fit or locked into apertures 49 in a manner to irremovably couple the enclosure means and the cap.

In using the device of the invention, cap 30 is removed and a syringe or other aspiration-type device 28 is connected to the upper portion 26a of the supporting means in the manner shown in FIG. 5. The device is then mated with the injection site 12 by placing the skirt-like shroud portion 32 over the injection site so that legs 34a of the bayonet slots are aligned with the tubes 24 and then exerting a downward pressure on the device sufficient to cause needle 18 to penetrate the septum in the manner shown in FIG. 6. The device is then rotated so that tubes 24 move into curved portions 34b of bayonet slots 34. This will securely lock the device in position over the injection site with the penetrating member, or needle 18, in communication with chamber 17 of the injection site. Fluids can now be injected into or withdrawn from chamber 17 in a manner well known to those skilled in the art.

When the sampling or injection procedure is completed, the device is once again rotated to a position wherein tubes 24 align with legs 34a of the bayonet slot. With the device in this position, an upward force exerted on the device will permit the needle 18 to be withdrawn from the septum. To prevent accidental needle stick or contamination of the user, the closure means is immediately interlocked with the shroud by inserting shroud portion 32 into the closure member 40 in the manner shown in FIG. 3. It is to be noted that with the closure means in the position shown in FIG. 3, the end of the penetrating member is sealably received within counterbore 43b thereby preventing any flow of blood or other fluid from the penetrating member into the closure means. A downward force exerted in the direction of the arrow 50 of FIG. 9 will cause legs 48 to crush in the manner illustrated in FIGS. 8 and 9. As the legs crush, walls 42 will be yieldably deformed outwardly and locking rim 44 will snap over shoulders 46 in the manner shown in FIG. 10. Once rim 44 has snapped over locking shoulder 46, the closure member will be permanently locked to the shroud in a manner such that needle 18 and any contamination carried thereby is completely and safely encapsulated within the shroud and column 43a of the cap-like member 40. Finally, upper closure cap 30 is locked in position over the upper portion 26a of the supporting means. With cap 30 in position, all contaminates carried by the penetrating member of the device are completely and safely contained so that the device can be safely transported for disposal.

Referring now to FIGS. 11 through 14, another form of the safety enclosure of the present invention is there illustrated. This form of the enclosure is similar in many respects to that previously described and like numerals are used to describe like components. However, this form of the enclosure is designed for use in conjunction with an injection site 62 of the character shown in FIG. 11. This injection site is similar in most respects to the previously identified injection site 12 and comprises a body portion within which is mounted a septum 66. Septum 66 is of a character having cannula access means such as a sealable aperture or, as shown in FIG. 13, having a diametrically extending slit 65 adapted to receive a penetrating member, such as a blunt cannula of the character shown in FIG. 11 and identified by the numeral 68. Cannula 68 penetrates septum 66 in the manner shown in FIGS. 12 and 14. As best seen in FIG. 12, body portion 64 includes a hollow chamber 70 which is of a slightly different, curved bottom configuration which is accessible via the septum by a cannula 68. Chamber 70 has first and second ports 72 and 74 each of which is connected to a length of tubing 76. As previously mentioned, injection site 62 is of a character well known to those skilled in the art.

The embodiment of the safety enclosure illustrated in FIGS. 11 through 14, comprises supporting means, generally designated by the numeral 78, for rigidly supporting the penetrating means or cannula 68 which is of standard design having a central fluid passageway 80. Operably associated with the supporting means for conducting fluid toward and away from the fluid passageway 80 is a fluid flow means shown in FIG. 11 as a Luer lock syringe 82 or similar type of aspiration device which is readily mateable over the generally tubular shaped upper end 78a of supporting means 78. Prior to and following use of the device of the invention, the upper end 78a of the closure means can be closed by a removable cap 30 of the character shown in FIGS. 1 and 2.

The lower portion of the supporting means 78 comprises enclosure means for enclosing cannula 68 and for releasably interconnecting the device with the lengths of tubing 76 which lead to the injection site 62. The enclosure means is of the character previously described and includes a skirt-like shroud 32 having oppositely disposed, bayonet-like, P-shaped, tube-receiving apertures 34. Apertures 34 comprise the interconnection means of the form of the invention for interconnecting the device to the tubes 76, are sized so that tubes 76 can be closely received therewithin in the manner previously described to releasably interlock the device with tubes 76. Disposed intermediate upper portion 78a and skirt portion 32 is a pair of oppositely disposed, outwardly-extending gripping members 36 which can be gripped by the fingers of the user to facilitate rotation of the apparatus into and out of the locking position and into the non-removable cap.

Referring now to FIGS. 15 through 23, still another form of the safety enclosure of the present invention is there illustrated. This form of the enclosure is designed for use in conjunction with an injection site 102 of the character shown in FIG. 20 which comprises a body portion 104 within which is mounted a septum 106. As best seen in FIG. 22, body portion 104 includes a hollow chamber 107 which is accessible via the septum by a penetrating means such as or a hollow needle 108. Chamber 107 has first and second ports 120 and 122 each of which is connected to a length of tubing 124. As previously mentioned, the injection site 102 is more fully illustrated and described in U.S. Pat. No. 4,763,648, which Patent is hereby incorporated herein by reference.

The embodiment of the safety enclosure illustrated in FIGS. 15 through 23, comprises supporting means, generally designated by the numeral 126, for rigidly supporting the penetrating means, such as penetrating member, here shown as a hollow needle 108 of standard design having a central fluid passageway. Operably associated with the supporting means for conducting fluid toward and away from the fluid passageway of needle 108 is a fluid flow means shown in FIG. 20 as a conventional syringe 28, the end of which is closely receivable within the upper end 126a of supporting means 126. Prior to and following use of the device of the invention, the upper end 126a of the closure means can be closed by a removable cap 130 of the character shown in FIGS. 15 and 16.

The lower portion of the supporting means 126 comprises enclosure means for enclosing needle 108 and for releasably interconnecting the device with the lengths of tubing 124 which lead to the injection site 102. The enclosure means is somewhat similar to that previously described and includes a skirt-like shroud 132 having oppositely disposed, bayonet-like, P-shaped, tube-receiving apertures 134. Apertures 134 have an axially-extending leg portion 134a which is in communication with a curved portion 134b. Portions 134a and 134b, which comprise the interconnection means of the invention for interconnecting the device to the tubes 124, are sized so that tubes 124 can be closely received first within leg portions 134a and then, upon rotation of the skirt portion, within curved portions 134b in a manner to releasably interlock the device with tubes 124. Disposed intermediate upper portion 126a and skirt portion 134 is a pair of oppositely disposed, outwardly-extending gripping members 136 which can be gripped by the fingers of the user to facilitate rotation of the apparatus into the locking position shown in FIG. 21.

Forming an important feature of the apparatus of this latter form of the invention is closure means for interconnection with the shroud portion of the enclosure means in a manner to completely and safely enclose the penetrating member such as needle 108, which may be contaminated after the sampling operation. In the present form of the invention, the closure means comprises a cap member 140 having interconnected side and bottom walls 142 and 144 respectively (FIG. 16). Provided on wall 142 are circumferentially extending oppositely disposed sloping ramps 144 and a pair of circumferentially spaced locking members 146, which comprise the locking means of the present invention for permanently interlocking the closure means with skirt 132. A series of circumferentially spaced alignment elements 147 are also provided on wall 142, the lower extremities of which terminate along the upper surfaces of ramps 144 (FIG. 16).

As best seen in FIGS. 16 and 19, the enclosure means portion of the device is provided with two rows of circumferentially-spaced, oppositely-disposed, ratchet-like teeth 148 which are adapted to lockably engage locking members 146. As best seen in FIG. 19, teeth 148 and locking members 146 are sloped so that, as cap member 140 is rotated in a first clockwise direction, the teeth will readily slide over the locking members. However, due to the configuration of the locking members and the teeth as illustrated in FIG. 19, rotation of the cap member in the opposite direction will be blocked, thereby locking the cap member and the enclosure means together in the manner shown in FIG. 19.

As best seen by referring to FIGS. 16 and 19, a pair of arcuately shaped viewing slots 150 and 152 are provided in bottom wall 143 through which the rows of teeth and the locking members are visible. Slot 150 includes a widened portion 150a which is located proximate end 144a of one of the ramps 144 Extending radially outwardly from skirt portion 132 of the enclosure means are a pair of ramp engaging protuberances 154. Protuberances 154 and rows of teeth 148 are strategically spaced circumferentially of skirt 132 so that they will closely fit between the ends of the circumferentially spaced ramps 144 provided on cap wall 142 during initial mating of the enclosure means with the cap. Additionally, as indicated in FIGS. 16 and 17, side wall 142 is also provided with guide means shown here as a longitudinally extending guide slot 142a which is adapted to receive one row of teeth during the initial mating step so as to assist in the correction orientation of skirt 132 within respect to cap 140. Further, bottom wall 143 is provided with orientation means in the form of an upstanding cylindrically shaped stub wall 156, the diameter of which is slightly greater than the diameter of skirt portion 132. The orientation means, or stub wall 156 centers the enclosure means and, along with protuberances 154, orients the skirt and cap so as to guide teeth 148 into proper mating alignment with locking members 146 as the skirt is rotated relative to the cap. Stub wall 156 also function to contain fluid leakage and any contaminated blood or other fluid that may flow from the needle 108. In summary, three features of the device assure proper mating of the skirt and the cap, namely slot 142a, upstanding wall 156, and the strategic spacing of ramps 144.

In using the device of the invention, cap 130 is removed and the syringe or other aspiration type device, is interconnected with the upper portion 126a of the supporting means in the manner shown in the drawings. Chamber 107 of the injection site 102 is then accessed by placing the skirt-like shroud portion 132 over the injection site so that legs 134a of the bayonet slots ar aligned with the tubes 124 and then exerting a downward pressure on the device sufficient to cause needle 108 or other penetrating means to penetrate the septum in the manner shown in FIG. 22. Needle 108 may be coated with siliconé or like material to assist the penetration of the needle into the septum and its easy removal therefrom. The device is then rotated so that tubes 124 move into curved portions 134b of bayonet slots 134. This will securely lock the device in position over the injection site with the penetrating member, or needle 108 in communication with chamber 107 of the injection site. Fluids can now be injected into or withdrawn from chamber 107 using the previously identified fluid flow means in a manner well known to those skilled in the art.

When the sampling or injection procedure is completed, the device is once again rotated to a position wherein tubes 124 align with legs 134a of the bayonet slot. With the device in this position, an upward force exerted on the device will permit the needle 108 to be withdrawn from the septum. To prevent accidental needle stick or contamination of the user, the closure means is immediately interlocked with the enclosure means by inserting skirt portion 132 into the closure member or cap 140 in the manner shown in FIG. 17. Using slot, 142a as a guide, skirt or shroud portion 132 can be readily mated with member 140 so that the oppositely disposed rows of teeth and protuberances will be closely received between the ends of the two oppositely disposed ramps 144. The cap member 140 is then gripped so that the fingers of one hand engage the outside ribs 160 formed on wall 142 (FIG. 16). The enclosure means is then rotated relative to cap 140 in a clockwise direction by gripping wing-like members 136 with the fingers of the other hand. As rotation proceeds, the rows of teeth will move along the under surface of the ramps 144 to a position where the lead teeth of each row engage locking members 146. At this position, protuberances 154 will have also moved into engagement with the lower surface of the ramps 144. As shown in the lower portion of FIG. 16, ramps 144 are sloping so that protuberances 154 frictionally engage the lower ramp surface in a manner to progressively resist counter-rotational movement tending to separate the assemblies as the rows of teeth are moved toward the locking members 146. When the lead tooth in each row of the teeth engages the locking member adjacent thereto, an additional rotational force must be exerted sufficient to cause the first tooth to ride over the locking member with which it is engaged. A sustaining of this rotational force will then cause the second and third teeth to sequentially ride over the locking member until the parts reach the fully locked orientation shown in FIG. 19 wherein the leading tooth engages stops 161 provided on cap 140 (FIG. 19). In this position, the cap is locked against counter-rotation, and the cap is securely and irremovably locked together with the enclosure means thereby disenabling the device. This locked position can be verified by viewing the teeth through the viewing slots 150 and 152 provided in the bottom wall of the closure cap (FIG. 19). Further insuring complete locking even in darkness or poor light is the clearly audible clicking sound produced as each tooth passes over the locking member.

Having now described the invention in detail in accordance with the requirements of the patent statutes, those skilled in the art will have no difficulty in making changes and modifications in the individual parts or their relative assembly in order to meet specific requirements or conditions. Such changes and modifications may be made without department from the scope and spirit of the invention as set forth in the following claims.

I claim:

1. An enclosure for use in conjunction with an injection site comprising a body portion including a chamber accessible via a septum by a penetrating member, such as a cannula, having a fluid passageway, said chamber having first and second fluid ports each connected to a length of tubing, said enclosure comprising;
   (a) supporting means for rigidly supporting the penetrating member;
   (b) fluid flow means operably associated with the penetrating member for conducting fluid toward and away from the fluid passageway of the penetrating member;
   (c) enclosure means connected to said supporting means for enclosing the penetrating member, said enclosure means including a shroud portion receivable over the body portion of the injection site;
   (d) closure means for closing said shroud portion in a manner to encapsulate the penetrating member therewithin, said closure means comprising a closure member having a yieldably deformable side wall; and
   (e) locking means for lockably interconnecting said closure means with said supporting means, said locking means comprising a shoulder provided on said shroud portion of said enclosure means and a radially inwardly protruding locking member provided on said closure means for locking engagement with said shoulder, said locking member comprising a circumferentially extending shoulder provided on said side wall, said side wall further having spacer means for preventing accidental interlocking of said closure member with said enclosure means.

2. An enclosure as defined in claim 1 in which said closure member includes a bottom wall having means for sealably receiving said penetrating member to block fluid flow therefrom.

3. An enclosure as defined in claim 2 in which said means for receiving said penetrating member comprises an upstanding column having a counterbore therein.

4. An enclosure for use in conjunction with an injection site, said injection site comprising a body portion including a chamber accessible via a septum by a penetrating member having a fluid passageway, said chamber having first and second fluid ports each connected to a length of tubing, said enclosure comprising:
   (a) supporting means for rigidly supporting the penetrating member;
   (b) fluid flow means operably associated with the penetrating member for conducting fluid toward and away from the fluid passageway of the penetrating member;
   (c) enclosure means connected to said supporting means for enclosing the penetrating member, said enclosure means including a shroud portion receivable over the body portion of the injection site, said shroud portion having a plurality of teeth and including circumferentially spaced protuberances;
   (d) closure means for closing said shroud portion in a manner to encapsulate the penetrating member therewithin, said closure means including a locking element and comprising a cap-shaped member having a side wall receivable over said shroud portion and being provided with circumferentially spaced locking members engageable by said teeth upon relative rotation of said shroud portion and said cap-shaped member and also being provided with circumferentially spaced ramps engageable by said protuberances upon relative rotation of said shroud portion and said cap-shaped member; and
   (e) locking means for lockably interconnecting said closure means with said supporting means, said locking means comprising at least one locking element provided on said shroud portion for locking engagement with said locking element provided on said closure means upon relative rotation of said shroud and said closure means.

5. An enclosure as defined in claim 4 further including interconnection means for releasably interconnecting said enclosure means with the lengths of tubing when said shroud portion is received over the body portion of the injection site.

6. An enclosure for use in conjunction with an injection site, said injection site comprising a body portion including a chamber accessible via a septum by a penetrating member having a fluid passageway, said chamber having first and second fluid ports each connected to a length of tubing, said enclosure comprising:
   (a) supporting means for rigidly supporting the penetrating member;
   (b) fluid flow means operably associated with the penetrating member for conducting fluid toward and away from the fluid passageway of the penetrating member;
   (c) enclosure means connected to said supporting means for enclosing the penetrating member, said enclosure means including a shroud portion receivable over the body portion of the injection site, said shroud portion being provided with a protuberance and having a plurality of locking teeth extending therefrom;

(d) closure means for closing said shroud portion in a manner to encapsulate the penetrating member therewithin said closure means comprising a closure member having interconnected side and bottom walls, said side wall having a locking member engageable by said locking teeth upon relative rotation of said shroud portion and said closure member, said side wall of said closure member being provided with a ramp engageable by said protuberance for guiding said locking teeth into engagement with said locking member.

7. An enclosure as defined in claim 6 in which said shroud portion of said enclosure means is provided with first and second circumferentially spaced rows of locking teeth and in which said side wall of said closure member is provided with first and second locking members engagable respectively by said first and second rows of locking teeth upon relative rotation of said shroud relative to said closure member.

8. An enclosure as defined in claim 7 in which said locking teeth and said locking members are configured to permit limited rotation of said shroud relative to said closure member in one direction and to block rotation in the opposite direction whereby, upon engagement of said locking teeth with said locking members, said closure member is irremovably connected to said shroud.

9. An enclosure as defined in claim 7 in which said bottom wall of said closure member includes an upstanding wall defining a chamber for containing fluids leaking from said penetrating member.

10. An enclosure as defined in claim 7 further including interconnection means for releasably interconnecting said enclosure means with the length of tubing when said shroud portion is received over the body portion of the injection site.

11. An enclosure for use in conjunction with an injection site, said injection site comprising a body portion including a chamber accessible via a septum by a penetrating member having a fluid passageway, said chamber having first and second fluid ports each connected to a length of tubing, said enclosure comprising:
  (a) supporting means for rigidly supporting the penetrating member;
  (b) fluid flow means operably associated with the penetrating member for conducting fluid toward and away from the fluid passageway of the penetrating member;
  (c) enclosure means connected to said supporting means for enclosing the penetrating member, said enclosure means including a shroud portion receivable over the boy portion of the injection site, said shroud portion being provided with a ramp engaging element and having a plurality of locking elements;
  (d) closure means for closing said shroud portion in a manner to encapsulate the penetrating member therewithin, said closure means comprising a closure member having interconnected side and bottom walls, said side wall having a locking member engageable by said locking elements upon relative rotation of said shroud portion and said closure member, said side wall of said closure member being provided with a ramp engageable by said ramp engaging element for guiding said locking elements into engagement with said locking member.

* * * * *